(12) United States Patent
Honda et al.

(10) Patent No.: US 9,488,596 B2
(45) Date of Patent: Nov. 8, 2016

(54) DEFECT INSPECTION METHOD AND DEVICE FOR SAME

(71) Applicant: Hitachi High-Technologies Corporation, Minato-ku, Tokyo (JP)

(72) Inventors: Toshifumi Honda, Tokyo (JP); Yuta Urano, Tokyo (JP); Hisashi Hatano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/978,372

(22) Filed: Dec. 22, 2015

(65) Prior Publication Data

US 2016/0109382 A1    Apr. 21, 2016

Related U.S. Application Data

(63) Continuation of application No. 14/359,221, filed as application No. PCT/JP2012/077234 on Oct. 22, 2012, now Pat. No. 9,255,888.

(30) Foreign Application Priority Data

Nov. 24, 2011  (JP) ................................ 2011-256483

(51) Int. Cl.
  *G01N 21/95*  (2006.01)
  *G01N 21/956*  (2006.01)
  *G01N 21/88*  (2006.01)

(52) U.S. Cl.
  CPC ...... *G01N 21/9501* (2013.01); *G01N 21/8851* (2013.01); *G01N 21/956* (2013.01); *G01N 2201/06* (2013.01)

(58) Field of Classification Search
  CPC ..................... G01N 21/9501; G01N 21/8851; G01N 21/956; G01N 2201/06
  USPC ................. 356/237.1–237.5; 250/359, 336.1
  See application file for complete search history.

(56) References Cited

U.S. PATENT DOCUMENTS 5,541,416 A    7/1996  Washizuka
5,903,342 A *  5/1999  Yatsugake .............. G01N 21/94
                                        250/559.41

(Continued)

FOREIGN PATENT DOCUMENTS

JP    02-080942 A    3/1990
JP    09-304289 A   11/1997

(Continued)

OTHER PUBLICATIONS

Hamamatsu: MPPC Multi-Pixel Photon Counter, Aug. 2007.

(Continued)

*Primary Examiner* — Sang Nguyen
(74) *Attorney, Agent, or Firm* — Miles & Stockbridge P.C.

(57) ABSTRACT

In defect scanning carried out in a process of manufacturing a semiconductor or the like, a light detection optical system comprising a plurality of photosensors is used for detecting scattered light reflected from a sample. The photosensors used for detecting the quantity of weak background scattered light include a photon counting type photosensor having few pixels whereas the photosensors used for detecting the quantity of strong background scattered light include a photon counting type photosensor having many pixels or an analog photosensor. In addition, nonlinearity caused by the use of the photon counting type photosensor as nonlinearity of detection strength of defect scattered light is corrected in order to correct a detection signal of the defect scattered light.

8 Claims, 12 Drawing Sheets

(56) References Cited

U.S. PATENT DOCUMENTS

| | | | |
|---|---|---|---|
| 6,064,477 A * | 5/2000 | Matsumoto | G01N 21/94 356/237.2 |
| 8,514,388 B2 * | 8/2013 | Maruyama | G01N 21/47 356/237.1 |
| 8,670,116 B2 | 3/2014 | Nakao et al. | |
| 8,922,764 B2 * | 12/2014 | Urano | G01N 21/956 356/237.1 |
| 2004/0207836 A1 * | 10/2004 | Chhibber | G01N 21/4738 356/237.4 |
| 2005/0185172 A1 | 8/2005 | Ishimaru et al. | |
| 2006/0067471 A1 | 3/2006 | Hopkins et al. | |
| 2006/0256325 A1 | 11/2006 | Mcmillan et al. | |
| 2009/0009753 A1 | 1/2009 | Horai et al. | |
| 2009/0290168 A1 | 11/2009 | Hamamatsu et al. | |
| 2010/0004875 A1 * | 1/2010 | Urano | G01N 21/4738 702/40 |
| 2010/0060895 A1 | 3/2010 | Oshima et al. | |
| 2012/0194807 A1 | 8/2012 | Maruyama et al. | |
| 2013/0114073 A1 * | 5/2013 | Namba | G01J 1/10 356/226 |
| 2013/0286385 A1 | 10/2013 | Miyazaki et al. | |
| 2013/0313442 A1 | 11/2013 | Wang et al. | |
| 2013/0321798 A1 | 12/2013 | Urano et al. | |

FOREIGN PATENT DOCUMENTS

| | | |
|---|---|---|
| JP | 2000-046734 A | 2/2000 |
| JP | 2006-201179 A | 8/2006 |
| JP | 2010-014635 A | 1/2010 |
| JP | 2011-69659 A | 4/2011 |

OTHER PUBLICATIONS

Office Action for related Japanese Patent Application No. 2014-262004 (mailed Oct. 6, 2015).

* cited by examiner

DEFECT INSPECTION METHOD AND DEVICE FOR SAME

BACKGROUND

The present invention relates to a defect inspection method for inspecting an infinitesimal defect existing on the surface of a sample, identifying the type and dimensions of the defect, and outputting the result, and relates to a defect inspection device provided for the method.

In order to sustain and/or improve the yield of a product on a manufacturing line of a semiconductor substrate, the semiconductor substrate and the thin-film substrate or the like is inspected for a defect existing on the surface. Known documents describing conventional defect-inspection technologies include Japanese Patent Application Laid-Open No. Hei9-304289 (used as PTL 1), Japanese Patent Application Laid-Open No. 2006-201179 (used as PTL 2) and US Patent Application Ser. No. 2006/0256325 (used as PTL 3). In accordance with these technologies, in order to detect an infinitesimal defect existing on the surface of a sample, illumination light is converged to dimensions of several tens of microns and radiated to the surface. Then, scattered light from the defect is surface. Then, scattered light from the defect is converged and detected to inspect the surface for the defect having dimensions ranging from several tens of nanometers to at least several tens of microns. A stage for holding the sample (the object of inspection) is moved in a rotation and a parallel movement to scan the surface of the sample by making use of an illumination-light spot moving along a spiral-like path. In this way, the entire surface of the sample is inspected.

In addition, in accordance with the technologies described in PTLs 1 and 2, components of the scattered light from a defect are detected. To be more specific, the components are emitted in a large-angle direction and a small-angle direction. Then, the component ratio is used for identifying the type of the defect.

In addition, in accordance with the technology described in PTL 2, the dimensions of a detected defect are computed on the basis of the strength of scattered light from the defect.

In addition, in accordance with the technology described in PTL 3, in order to reduce a thermal damage incurred by the sample, while the object of inspection is being inspected, the power of the illumination light, the scanning velocity of the illumination-light spot or the dimensions of the illumination-light spot are controlled. To put it concretely, the thermal damage incurred by the sample is assumed to have a magnitude determined by the product of the illumination power density of the radiated light and the radiation time. Then, the power of the illumination light, the scanning velocity of the illumination-light spot or the dimensions of the illumination-light spot are changed in accordance with radial position of the illumination spot on the sample being scanned so that the magnitude of the thermal damage does not exceed a fixed value.

CITATION LIST

Patent Literature

PTL 1: Japanese Patent Application Laid-Open No. Hei9-304289

PTL 2: Japanese Patent Application Laid-Open No. 2006-201179

PTL 3: US Patent Application Ser. No. 2006/0256325

SUMMARY

The defect inspection carried out in a process to manufacture a semiconductor or the like imposes requirements described as follows. The defect inspection requires a capability of detecting an infinitesimal defect. In addition, the defect inspection requires that the dimensions of a detected defect be measured with a high degree of precision. In addition, the defect inspection requires that a sample be inspected in a non-destructive way. (That is to say, the defect inspection requires that a sample be inspected without changing the properties of the sample). In the case of the same sample serving as an object of inspections, the defect inspection requires that the inspection of the same sample always gives the same result of inspection (that is, the same number of detected defects, the same locations, the same dimensions and the same defect type). In addition, the defect inspection requires a capability of inspecting a number of samples within a fixed period of time.

In the technologies described in PTLs 1 and 2, particularly in the case of an infinitesimal defect with a dimension not greater than 10 nanometers, scattered light generated from the defect is extremely weak so that a defect signal is buried in noises of the detector. As a result, the defect cannot be detected. In order to expose the extremely weak scattered light, a detector having a high gain is used in many cases. Normally, an electronic multiplier is utilized. If a photomultiplier tube is used, however, the gain is increased and high-speed detection is carried out so that effects of dark current noises of the detector undesirably increase. In order to avoid this problem, illumination power is raised. In this case, however, the increase of the temperature of the sample rises so that the sample incurs a thermal damage. By the way, the increase of the temperature of the sample is caused by illumination light. As an alternative, in order to avoid it, the scanning speed of the sample is reduced. However, a reduced scanning speed decreases a sample area which can be inspected within a certain period or the number of samples which can be inspected within a certain period. The above description reveals that it is difficult to detect an infinitesimal defect at a high speed while avoiding thermal damages.

On the other hand, the technology described in PTL 3 is devised so that the amount of illumination light radiated to a unit area at any arbitrary position on the sample is fixed. In general, however, the amount of illumination light detected from a defect is proportional to the 6th power of the size of the defect. It is thus difficult to increase the light quantity in order to merely comply with this. As a result, the gain of the detector must be raised substantially.

There is known a photon counting method which is a method for detecting very weak light. In general, by carrying out photon counting on very weak light in order to count the number of photons detected from the light, the SN ratio of the signal can be improved. Thus, a stable signal can be obtained with a high degree of sensitivity and a high degree of precision. A known example of the photon counting method is described as follows. This method counts the number of pulse-current generations of pulse currents generated by incidence of photons to a photomultiplier tube or an avalanche photodiode. When a plurality of photons arrive during a short period of time, causing a plurality of pulse currents to flow, the number of pulse currents cannot be counted. Thus, the light quantity cannot be measured with a high degree of precision so that this method cannot be applied to inspection of defects.

In addition, another known typical photon counting method is explained as follows. The method employs an array sensor configured as a matrix of numerous avalanche photodiode pixels. Photons incident to each of the pixels generate pulse currents. Then, a sum of the pulse currents is found. A detector used in the method is called an Si-PM (Silicon Photomultiplier), a PPD (Pixeleted Photon Detector), an MPPC (Multi-Pixel Photon Counter) or the like. In accordance with a measurement method making use of this detector, unlike the single photomultiplier tube described earlier and a photon counter operating in a Geiger mode using avalanche photodiodes, the light quantity can be measured even for a case in which a plurality of photons are incident in a short period of time. In this method, the magnitude of the detection signal is measured from pulse counts each representing the number of pulses output by each of numerous detectors arranged into a matrix. Thus, in order to detect light quantities ranging from a small light quantity to a large light quantity, it is necessary to form a number of pixels in the detectors.

If a number of pixels are formed in this array sensor, however, the light detection efficiency in general decreases undesirably, raising a problem that the sensor is easily affected by shot noises. In this array sensor, it is necessary to provide an insensitive area on a boundary portion separating pixels from each other. Thus, since the pixel size decreases, the aperture ratio of the pixel is reduced. In an inspection method whereby illumination light is converged on the object of inspection and scattered light is detected in order to detect a defect, scattered light from the surface of the sample is detected. Thus, there are variations of light generated by the sensors. That is to say, the shot noises become one noise element. In order to reduce the shot noises, it is necessary to detect as many photons as possible. If the aperture ratio of the pixel decreases, however, the ratio of the shot noises to the signal increases so that the inspection sensitivity is reduced. If the number of pixels is raised, on the other hand, a countermeasure against the shot noises is improved but the linearity of the signal detection becomes poor. In particular, if strong light is radiated to the surface of the sample, the amount of scattered light from the surface of the sample also increases and the scattered light becomes background scattered light. Since many sensors output pulse signals, photons incident to the pixel are no longer detected from a small defect on the sample. That is to say, a phenomenon similar to that caused by a reduced sensor aperture ratio occurs, decreasing the sensitivity of the defect detection.

In order to solve the problems described above, the present invention provides a defect inspection device wherein a detection optical system for detecting scattered light reflected from a sample is configured to comprise a plurality of detectors. In the defect inspection device, a photon counting detector with few pixels is applied as a detector for detecting a small background scattered light quantity. In addition, a photon counting detector with many pixels is applied as a detector for detecting a large background scattered light quantity or an analog detector is applied. In addition, nonlinearity caused by applying the photon counting detectors as the nonlinearity of the detection strength of scattered light is corrected in order to correct the defect scattered light detection signal.

That is to say, in order to solve the problems described above, the defect inspection device provided by the present invention is configured to comprise: table unit on which a sample is mounted so that the sample can be moved; laser light source unit for radiating laser light; detection optical system for converging light reflected by the sample to which the laser light radiated by the laser light source unit is radiated; light detection unit for receiving the reflected light converged by the detection optical system and converting the light into an electrical signal; signal processing unit for receiving the signal output by the light detection unit receiving the reflected light, processing the signal and detecting a defect on the sample; size computation unit for computing the size of the defect detected by the signal processing unit; and output unit for outputting a result of processing carried out by the signal processing unit and the size computation unit to a display screen, wherein: the light detection means has a plurality of photosensors including a photon counting detector configured to comprise a plurality of pixels; and the size computation unit has a conversion section for correcting nonlinearity of the output of the photon counting detector employed in the light detection unit, the size computing unit computing the size of the defect by processing output signals of the plurality of photosensors employed in the light detection means, the output signals including a signal which has been output from the photon counting detector and has been corrected nonlinearity by the conversion section.

In addition, in order to solve the problems described above, the defect inspection method provided by the present invention is implemented by: radiating laser light to a sample mounted on a table moving in a parallel movement while rotating; converging light reflected by the sample to which the laser light is radiated; driving light detection unit to receive the converged light reflected by the sample and convert the light into an electrical signal; receiving the signal output by the light detection unit receiving the reflected light, processing the signal and detecting a defect on the sample; computing the size of the detected defect by processing the signal output by the light detection unit; and outputting information on the detected defect and information on the computed size of the detected defect to a display screen, wherein: the light detection unit has a plurality of photosensors including a photon counting detector configured to comprise a plurality of pixels whereas the photosensors each receive light reflected by the sample and convert the light into an electrical signal; and the size of the defect is computed by correcting nonlinearity of output from the photon counting detector, among signals output by the plurality of photosensors receiving light reflected by the sample, and processing each output signals of the plurality of photosensors, the output signals including an output signal of the photon counting detector whose nonlinearity has been corrected.

In accordance with the present invention, it is possible to detect both a small defect generating only very weak light and a deformed defect generating scattered light only at the backward.

DESCRIPTION OF THE PREFERRED EMBODIMENTS

Embodiments of the present invention are explained by referring to the diagrams as follows.

Figure 1:
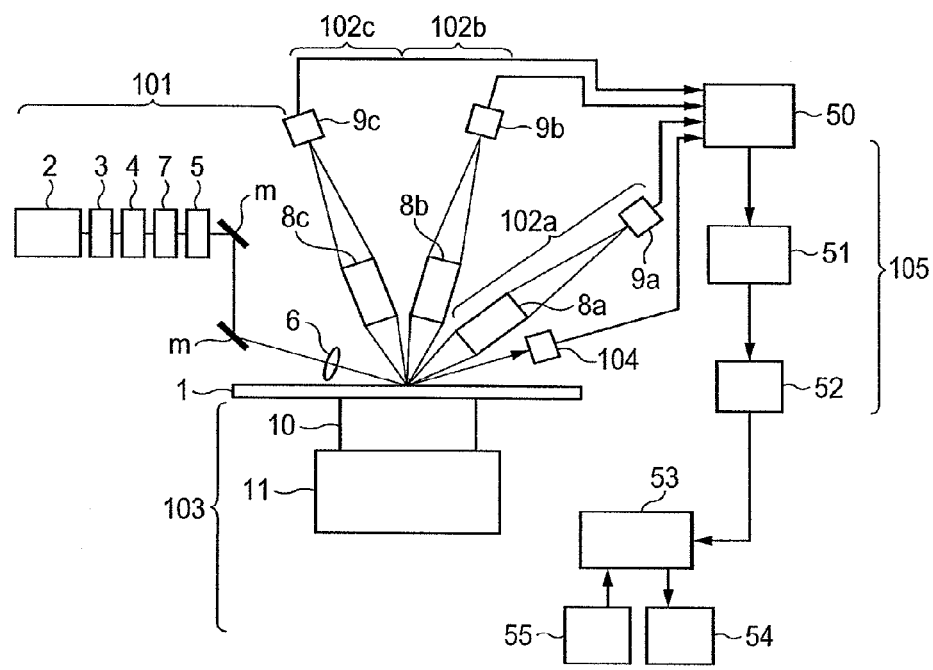
FIG. 1 is a block diagram showing an entire outline configuration of a defect inspection device according to an embodiment of the present invention.

The configuration of an embodiment of the present invention is explained by referring to FIG. 1. The embodiment is configured by installing an illumination section 101, a detection section 102 (102a, 102b and 102c), a stage 103 on which a sample 1 can be mounted, a signal processing section 105, an entirety control section 53, a display section 54 and an input section 55. The signal processing section 105 has an analog processing section 50, a defect determination section 51 and a defect-size-inference/defect-classification 52. If necessary, a regular-reflection light detection section 104 is provided for inspecting a defect having a large area or measuring the surface of the sample.

The illumination section 101 is configured to arbitrarily comprise a laser light source 2, an attenuator 3, a polarization device 4, a beam expander 7, an illumination distribution control device 5, a reflection mirror m and a convergence lens 6. A laser beam radiated from the laser light source 2 is adjusted by the attenuator 3 to a desired beam strength, adjusted by the polarization device 4 to a desired polarization state, adjusted by the beam expander 7 to a desired beam diameter and radiated to an inspection-object area of the sample 1 by way of the reflection mirror m and the convergence lens 6. The illumination distribution control device 5 is used for controlling an illumination strength distribution on the sample 1. FIG. 1 shows a configuration in which the illumination section 101 radiates light from an inclined position in a direction inclined with respect to the normal line of the sample 1. However, it is also possible to adopt a configuration in which light is radiated in a direction perpendicular to the surface of the sample 1. It is also possible to make use of switch means for changing the illumination optical path from that of the former configuration to that of the latter configuration and vice versa.

To detect a small defect close to the surface of the sample, as the laser light source 2, it is possible to employ a light source which oscillates a laser beam and has a high output of at least 1 W. The laser beam has a wavelength which is hardly capable of penetrating into the inside of the sample. Examples of such a laser beam are an ultraviolet laser beam having a short wavelength and a vacuum ultraviolet laser beam. To detect a defect in the sample, on the other hand, as the laser light source 2, it is possible to employ a light source which oscillates a laser beam having a wavelength capable of easily penetrating into the inside of the sample. Examples of such a laser beam are a visible laser beam and an infrared laser beam. In accordance with requirements, it is possible to arbitrarily select an inclined-direction illumination light source or a perpendicular-direction illumination light source.

Figure 2A:
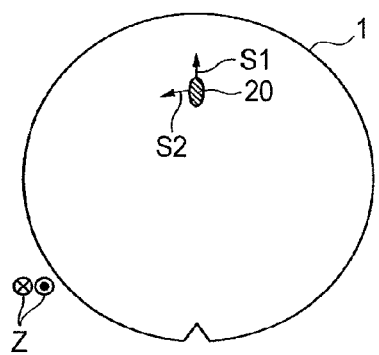
FIG. 2A is a sample top-view diagram showing an illumination area on a sample.
Figure 2B:
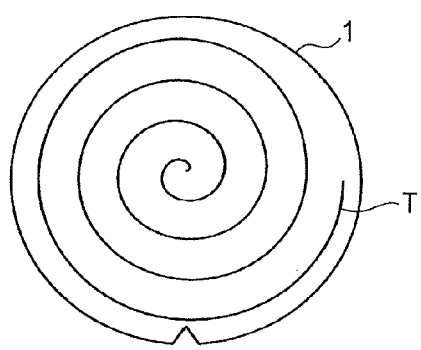
FIG. 2B is a sample top-view diagram showing an illumination locus on a sample.

The stage 103 comprises a translation stage 11, a rotation stage 10 and a Z stage (not shown in the figure). FIG. 2A shows an illumination area (illumination spot 20) on the sample 1. FIG. 2B shows a relation with a scanning direction of movements made by the rotation stage 10 and the translation stage 11 and shows a locus drawn on the surface of the sample 1 due to the movements as a locus of the illumination spot 20. FIG. 2A shows the shape of the illumination spot 20. The shape is an elliptical shape formed with the long axis oriented in a direction S1 and the short axis oriented in a direction perpendicular to the direction S1 as a result of illumination distribution control executed by the illumination section 101 or illumination from the inclined direction. As shown in FIG. 2B, due to a rotational movement made by the rotation stage 10, the illumination spot 20 is scanned in a circumferential direction S2 of a circle having the rotational axis of the illumination spot 20 as its center and, due to a translational movement made by the translation stage 11, the illumination spot 20 is scanned in a translational direction S1 of the translation stage 11. The illumination section 101 is configured so that the longitudinal direction of the illumination spot 20 is parallel to the scanning direction S1 and, due to scanning in the scanning direction S1, the illumination spot 20 passes through the rotational axis of the rotation stage 10. The movement of the Z stage determines the altitude of the sample 1. That is to say, the movement of the Z stage causes a movement in a direction normal to the surface of the sample 1.

In the above configuration, during one rotation of the sample in scanning in the scanning direction S2, scanning in the scanning direction S1 is carried out along a distance not longer than the longitudinal-direction length of the illumination spot 20. Thus, the illumination spot 20 draws a spiral locus T so that the entire surface of the sample 1 is scanned.

The detection sections 102a, 102b and 102c are configured to converge scattered light generated at azimuths different from each other and at elevation angles different from each other in order to detect the light. FIGS. 3A to 3D show typical configurations of the detection section 102a.

Figure 3A:
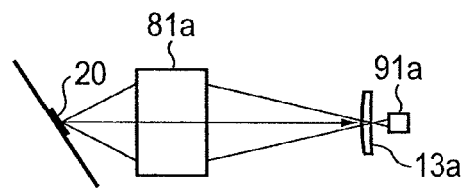
FIG. 3A is a front-view diagram showing the front view of a detection section having a configuration making use of an analog detection sensor.

FIG. 3A shows a typical configuration for a case in which an analog detection sensor is used. Since configuration elements of the detection sections 102b and 102c are identical with those of the detection section 102a, the configuration elements of the detection sections 102b and 102c are not explained. It is to be noted that, as will be described later by referring to FIGS. 4A to 4C, in order to detect scattered light in a wide angle range, the layout of the detection sections is not limited to that of the detection sections 102a, 102b and 102c shown in FIG. 1. It is preferable to provide a plurality of detection sections having detection directions different from each other at a number of locations.

As shown in FIG. 3A, the detection section 102a is configured to arbitrarily make use of a light convergence optical system 81a, a polarization filter 13a and a sensor 91a. The light convergence optical system 81a creates an image of the illumination spot 20 on a light receiving surface of the sensor 91a or in its vicinity. At the image creation location, a visual-field diaphragm (not shown in the figure) having a proper diameter is arbitrarily provided to eliminate or reduce background light generated from locations outside the illumination spot. The polarization filter 13a can be mounted on and dismounted from the optical axis of the light convergence optical system 81a and can be rotated at a light detection azimuth. The polarization filter 13a is intended to be a filter for reducing scattered light components caused by typically sample roughness which serves as a noise origin.

As the polarization filter 13a, it is possible to make use of a wire grid polarization plate or a polarization beam splitter, both having a high transmittance and a high extinction factor even for short wavelengths such as those of ultraviolet light. The wire grid polarization plate includes one having a structure created by fine fabrication of a metallic thin film such as an aluminum or a silver thin film on stripes. In order to make it possible to detect very weak foreign scattered light, a photomultiplier tube, an avalanche photodiode or a semiconductor photo detector coupled with an image intensifier is appropriately used. As the photomultiplier tube for realizing high sensitivity and high precision, it is desirable to make use of a photomultiplier tube of an ultra bi-alkali type or a super bi-alkali type. These types have a high quantization factor.

Figure 3B:
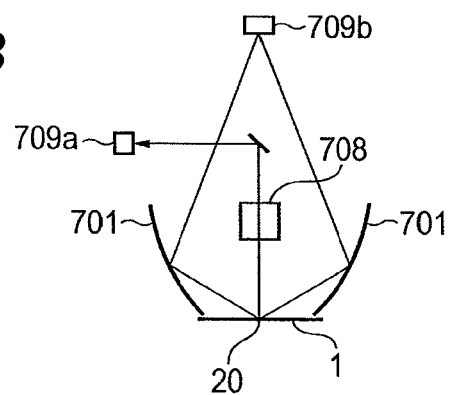
FIG. 3B is a front-view diagram showing the front view of a detection section having a configuration including a reflection optical system making use of an elliptical mirror.

FIG. 3B shows an example wherein a light convergence optical system comprising the detection section 102a, the detection section 102b and the detection section 102c which are shown in FIG. 1 is configured by a reflection optical system making use of one elliptical surface mirror 701. The light convergence optical system 701 is an elliptical surface mirror in which the first focal position of the ellipse serves as a radiation position of the illumination light whereas the second focal position of the ellipse is provided on a light receiving surface of a sensor 709b. The light convergence optical system 701 has a high NA including a shallow angle with respect to the surface of a wafer 1 and converges scattered light. Thus, the light convergence optical system 701 fits for guiding the light to the sensors 709a and 709b. In addition, there is provided a detection section comprising the light convergence optical system 701 and the sensors 709a and 709b. The detection section detects upward scattered light. Thus, there is provided a configuration capable of detecting light scattered in a plurality of directions at the same time.

Figure 3C:
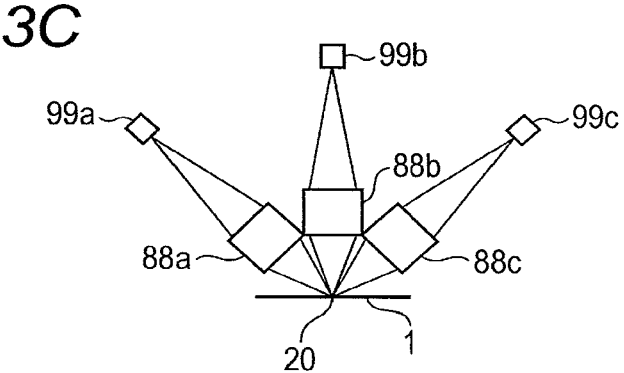
FIG. 3C is a front-view diagram showing the front view of a detection section having a configuration in which scattered light coming from a plurality of directions is converged to create an image on an image sensor.

FIG. 3C shows a typical configuration of a detection section for converging scattered light from a plurality of directions and creating an image on an image sensor. In the configuration, convergence image creation systems 88*a*, 88*b* and 88*c* create images on image sensors 99*a*, 99*b* and 99*c* from light scattered in a plurality of directions having different azimuths or different elevation angles.

By detecting scattered light from the surface of the sample 1, to which illumination light is radiated as an image and processing the image, it is possible to detect a defect generated in a circuit pattern on the sample 1 which can be a semiconductor wafer or a mask. Thus, the configuration is effective for scanning the sample on which the circuit pattern has been created. The image sensors 99*a*, 99*b* and 99*c* can be linear array sensors or 2-dimensional array sensors. The linear array sensors and the 2-dimensional array sensors are CCD or CMOS sensors. As an alternative, the image sensors 99*a*, 99*b* and 99*c* can also be sensitive image sensors made by connecting image intensifiers to the linear array sensors or the 2-dimensional array sensors. As another alternative, the image sensors 99*a*, 99*b* and 99*c* can also be a multi-anode photomultiplier tube.

Figure 3D:
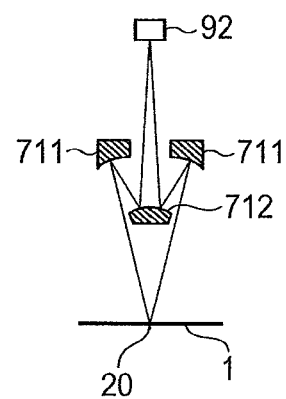
FIG. 3D is a front-view diagram showing the front view of a detection section having a configuration making use of a reflection optical system based on a Schwarzschild optical system.

FIG. 3D shows a typical configuration making use of a reflection optical system based on a Schwarzschild optical system. Among the scattered light generated by the illumination spot 20 shown in FIG. 1, the light reflected by a concave mirror 711 and converged by a convex mirror 712 is converged by an image sensor 92. This configuration is appropriate for a case in which illumination light having a short wavelength not exceeding 200 nm is radiated to the sample 1 and scattered light from the sample 1 creates an image on the image sensor 92.

Figure 4A:
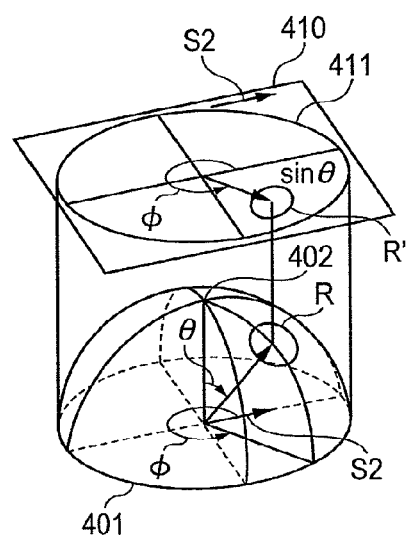
FIG. 4A is a celestial-sphere diagram showing an angle range in which scattered light from a sample is detected on the surface of the celestial sphere and a projection diagram showing the celestial-sphere diagram projected on a plane.
Figure 4B:
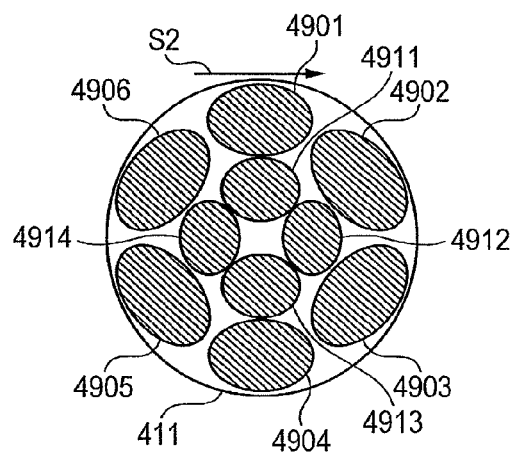
FIG. 4B is a sphere-surface front-view diagram showing a typical location of a detection section on the surface of the celestial sphere.
Figure 4C:
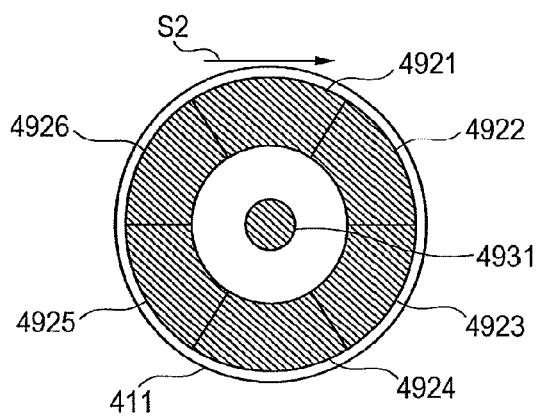
FIG. 4C is a sphere-surface front-view diagram showing another typical location of a detection section on the surface of the celestial sphere.

By referring to FIGS. 4B and 4C, the following description explains relations between angular components of scattered light detected by the detection sections 102*a*, 102*b* and 102*c*. FIG. 4A is an explanatory diagram to be referred to in description of a display method of a detected angle range. In FIG. 4A, an equatorial plane 401 corresponds to the surface of the sample 1 whereas the normal direction of the surface of the sample 1 is taken as the zenith 402 of a hemisphere. Reference symbol φ denotes an azimuth angle (longitude) taken the scanning direction S2 as a reference whereas reference symbol θ denotes an angle from the zenith. An angle range detected by the detection sections 102*a*, 102*b* and so on is shown as a region R on the hemisphere. It is shown in FIGS. 4B and 4C and denoted by reference numeral 411. It is obtained by parallel projection onto a plane 410 parallel to the equatorial plane. The angle ranges detected by the detection sections 102*a*, 102*b* and so on are shown as hatched portions. As is obvious from FIGS. 4B and 4C, a plurality of detection sections are provided to cover a wide angle range. It is thus possible to detect defects having a variety of types. In addition, depending on the defect type and the defect dimensions, the angle distribution of the defect scattered light varies. Thus, by making use of a plurality of detection systems to detect the strengths of scattered light beams having a variety of angles at the same time and by making use of a signal processing section to be described later to process the signals, it is possible to infer the type of the defect and the dimensions of the defect with a high degree of precision.

FIG. 4B shows a typical layout of a plurality of detection ranges including detection ranges 4901 to 4906 with low elevation angle directions and detection ranges 4911 to 4914 with high elevation angle directions. It shows a typical layout of a detection system for detecting foreign substances having small to large dimensions. If P polarization illumination is carried out, scattered light from a small foreign substance is radiated strongly in a low angle direction. By detecting low angle scattered light components over all azimuths of the detection ranges 4901 to 4906, a very small defect can be detected. In addition, by detecting scattered light components generated at high elevation angles in the detection ranges 4911 to 4914, a dent defect can also be detected with a high degree of sensitivity. An example of the dent defect is a COP (Crystal Originated Particle) which strongly generates scattered light at large angles. On the top of that, by placing a plurality of detectors in each of the θ and φ directions, it is possible to recognize the characteristic of a scattered light distribution which varies in accordance with the defect. FIG. 4C shows the position of a detection section for carrying out detection at all azimuths in detection ranges 4921 to 4926 in low elevation angle directions. The figure also shows the position of a detection section 4931 for detecting scattered light in the direction normal to the sample.

As a light convergence optical system 8, an elliptical surface mirror is used. As shown in FIG. 3B, the elliptical surface mirror makes use of an illumination spot position as one of the focal points. Thus, it is possible to converge scattered light of all azimuths in a specific θ angle range. In addition, by providing spatial filter means or optical path branch means on the optical path of the light convergence optical system, it is possible to collectively detect a plurality of corresponding detection sections. In either configuration, scattered light beams in a wide angle range are caught so that scattered light beams with generation directions varying in accordance with defects are detected. Thus, a variety of defects can be detected robustly. In addition, scattered light components in a plurality of directions are detected individually so that it is possible to classify defects by comparison with a scattered light distribution library to be described later and determine the dimensions of each defect.

The scattered light distribution of a defect depends on the property (index of refraction) of the defect, the shape of the defect and the dimensions of the defect. If the illumination light arrives in an inclined direction, as is commonly known, the larger the lateral dimension of the defect (the defect dimension in the in-plane direction of the sample surface), the more the scattered light slants in the forward direction. In this case, the forward direction is a direction close to the regular reflection direction of the illumination due to the surface of the sample. If the lateral dimension of the defect is extremely large in comparison with the wavelength of the illumination (that is, if the lateral dimension is at least 10 times the wavelength), most scattered light components are converged to the vicinity of the regularly reflected light. Thus, to catch a scattered light distribution of a defect with a large lateral dimension, detection of scattered light scattered in the vicinity of the regular reflection is effective.

Figure 5A:
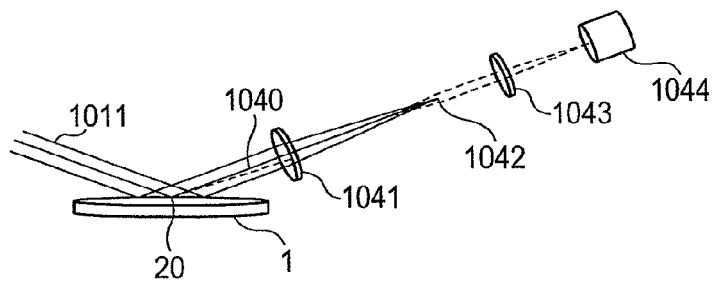
FIG. 5A is a front-view diagram showing the front view of a regular reflection light detection optical system having a configuration for optically blocking regularly reflected light by making use of a spatial filter in order to detect only scattered light in proximity to the regularly reflected light.
Figure 5B:
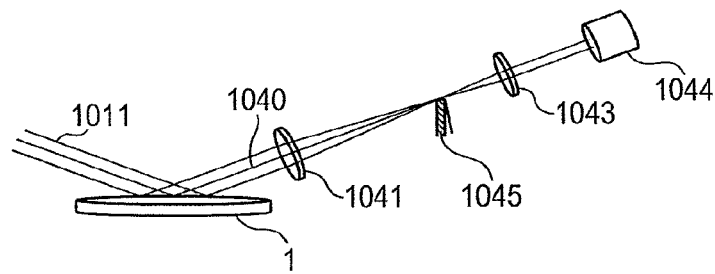
FIG. 5B a front-view diagram showing the front view of a regular reflection light detection optical system configured to include a detection system in accordance with the Schlieren method.
Figure 5C:
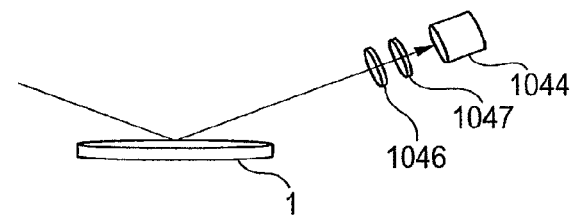
FIG. 5C is a front-view diagram showing the front view of a regular reflection light detection optical system having a configuration for carrying out ellipsometry processing for light regularly reflected by the surface of the sample.

FIGS. 5A to 5C show typical configurations of a regularly reflected light detection optical system section 104. FIG. 5A shows a configuration for optically blocking regularly reflected light from the surface of a sample 1 by making use of a spatial filter and for detecting only scattered light very close to the regularly reflected light. In this case, illumination light 1011 generated from the illumination section 101 is radiated to the surface of the sample 1. A lens 1041 is provided in such a way that the optical axis of the lens 1041 coincides with the optical axis 1040 of regularly reflected light from the sample 1 subjected to radiation of illumination light from the illumination section 101 (refer to FIG. 1) whereas the focal point of the lens 1041 coincides with the illumination spot 20. Light coming from the illumination spot 20 and passing through the lens 1041 becomes parallel light beams. A light blocking filter 1042 provided on the optical axis of the lens 1041 optically blocks regularly reflected light from the surface of the sample 1. Light comes from the illumination spot 20, slanting with respect to the regularly reflected light. The slanting light passes through a position separated away from the optical axis by a distance depending on the slanting angle. Thus, only a particular light component, which has a polarization angle not smaller than an angle corresponding to the size of the light blocking filter, passes through the light blocking filter, is converged by a lens 1043, and is detected by a sensor 1044. In the configuration described above, the regularly reflected light is optically blocked and the strength of a scattered light component close to the regularly reflected light is measured. It is to be noted that, by placing a division sensor, such as a four-division sensor, having a plurality of pixels at a position right behind the light blocking filter 1042, it is possible to measure the distribution of the scattered light close to the regularly reflected light.

FIG. 5B shows a typical configuration of a detection system based on the Schlieren method. The configuration shown in FIG. 5B can be obtained by replacing the light blocking filter 1042 of the configuration shown in FIG. 5A with a knife edge 1045. Slight polarization and slight diffusion of regularly reflected light caused by a defect having a size ranging from 1/10 times the dimension of the illumination spot to an equivalent size or an even larger size can be detected as a change in detection strength at a sensor 1044.

FIG. 5C shows a typical configuration for carrying out ellipsometry processing for light regularly reflected from the surface of the sample. There are a variety of techniques for carrying out the ellipsometry processing. In the case of this configuration, however, a phase element 1046 and a phase element 1047 are rotated at rotational speeds different from with each other and then the strength of transmitted light is detected by a sensor 1044. In this configuration, the polarization state of the regularly reflected light is completely measured so that, on the basis of a polarization-state change before and after the reflection occurring on the sample surface with illumination light, a complex refraction index of the sample surface and the film thickness can be computed.

Figure 6A:
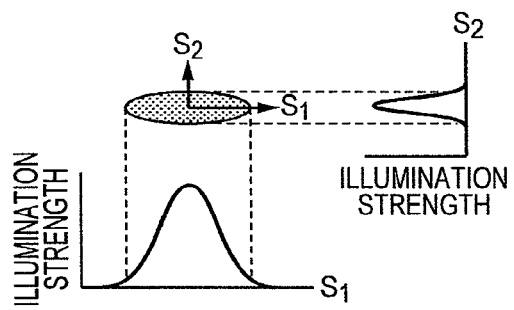
FIG. 6A showing the shape of an illumination spot on the surface of a sample 1 and graphs representing detection-signal profiles in S1 and S2 directions inside the illumination spot.
Figure 6B:
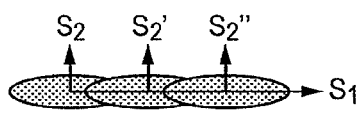
FIG. 6B is a front-view diagram showing the front view of the shape of 3 illumination spots on the surface of a sample 1 in a state wherein the half portions of all the illumination spots overlap each other.
Figure 6C:
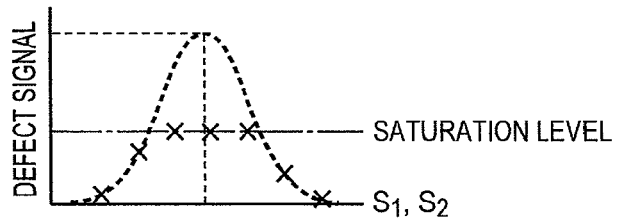
FIG. 6C is a graph representing a typical signal for a case in which the same defect has been detected a plurality of times.

FIGS. 6A to 6C are referred to in explaining the elimination of variations caused by a strength distribution of an illumination spot as variations of the defect scattering strength and explaining a countermeasure against saturation of the signal. In order to converge a light beam generated by a laser light source 2 (refer to FIG. 1) with a high degree of efficiency and create a small illumination spot on the surface of the sample, as the laser light source 2, a light source essentially generating a Gauss beam is used. Thus, an illumination strength distribution at the illumination spot 20 on the surface of the sample 1 is a Gauss distribution (Refer to FIG. 6A). If the scanning distance in the S1 direction per scanning rotation made in the S2 direction is shorter than the length of the illumination spot in the S1 direction, as shown in FIG. 6B, the illumination spot 20 is scanned to result in a state of overlapping in the S1 direction. At that time, the same defect is scanned a plurality of times with the defect position relative to the illumination spot 20 being changed. Thus, the signal of the same defect is detected a plurality of times. If the signal is plotted with the S1 direction taken as the direction of the horizontal axis, a Gauss distribution identical with the illumination strength distribution is drawn. Also with regard to the S2 direction, the signal is sampled in S2-direction scanning for a period shorter than a period during which the illumination spot is passing through a defect. Thus, by the same token, a signal detected a plurality of times from the same defect draws a Gauss distribution identical with the illumination strength distribution in the S2 direction.

FIG. 6C shows a typical signal for a case in which the signal of the same defect has been detected a plurality of times. A point denoted by an X mark is an actually obtained signal. This graph is a saturated example because the signal obtained when the defect passes through the center portion of the Gauss distribution, that is, the center portion of the illumination strength distribution, exceeds the saturation level of the detector. In addition, even if no saturation occurs, the detection signal of the defect has variations dependent on a relative position passed through by the defect in the illumination spot scanning. In such a case, since the original Gauss distribution (equivalent to the illumination strength distribution) is known, a true defect signal (a dotted line shown in FIG. 6C) can be recovered from a plurality of obtained signals. By adoption of such a method, it is possible to reduce defect signal variations caused by an illumination strength distribution and effects of the signal saturation. It is to be noted that the illumination strength distribution is not necessarily limited to a Gauss distribution. That is to say, a homogenizer or the like can also be used to create an all but uniform illumination strength distribution.

Figure 6D:
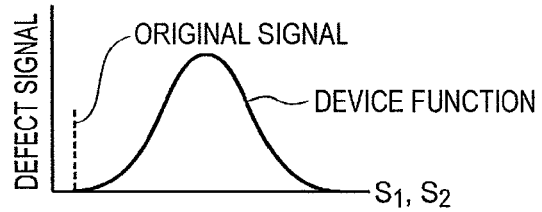
FIG. 6D is a graph representing the profile of a detection signal in which a device function has been convolved in an original signal.
Figure 6E:
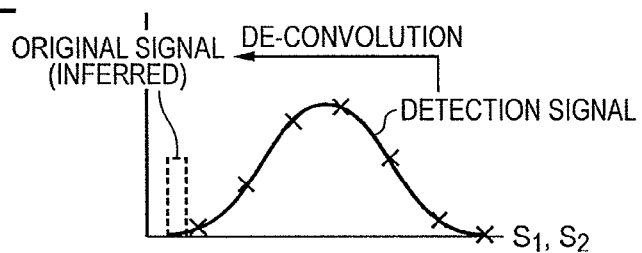
FIG. 6E is a graph representing a profile obtained as a result of deconvolution by a device function for the profile of a detection signal.

Next, a method for measuring spatial broadening of a defect with a high degree of precision is explained by referring to FIGS. 6D and 6E. Since the scanning speed is assured, the size of the illumination spot is increased to a large value of the order of several tens of microns. On the other hand, the defect is regarded as a point having no area. As described earlier, however, in the case of a defect having a lateral dimension of at least 10 times the wavelength (a lateral dimension of at least several microns), since the scattered light is converged to an almost regular reflection direction vicinity, information obtained from a scattered light distribution is little so that classification may be difficult. For such classification and such a dimension measurement, utilization of particular information, which indicates the number of sampling operations to detect the signal in scanning, is effective. As shown in FIG. 6D, however, the profile of the detection signal has a shape obtained by convolution of a instrumental function into the original signal (spatial broadening of the defect). Thus, the instrumental function limits the resolution of the measurement of the defect spatial broadening. In order to solve this problem, as shown in FIG. 6E, the profile (a dotted line shown in FIG. 6C) obtained by deconvolution carried out on the profile of the detection signal by making use of the instrumental function is used as an index. Thus, it is possible to measure the spatial broadening of the defect at a high resolution. In this case, the instrumental function means signal spreading caused by the illumination, detection and processing systems. In the configuration of this device, the instrumental function is equal to the illumination strength distribution. If the response speed of the detector or the processing system is low for signal sampling, the signal rounding caused by the low speed is also reflected in the instrumental function. The instrumental function is capable of carrying out actual measurement by measuring the detection signal profile of a defect having no spatial broadening (a defect considered to be a point).

Figure 7A:
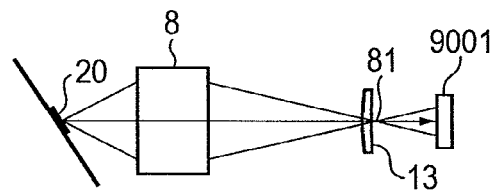
FIG. 7A is a diagram showing a typical configuration of a detection section for a case in which a photon counting sensor is used and is also a front-view diagram showing the front view of the detection section having a configuration in which the photon counting sensor is placed at a location shifted from a light convergence point of a light convergence optical system.
Figure 7B:
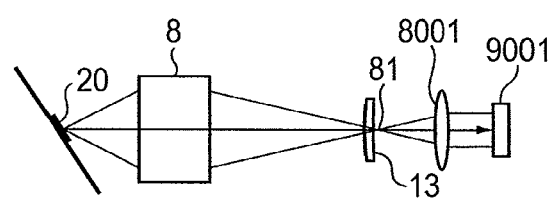
FIG. 7B is a diagram showing a typical configuration of a detection section for a case in which a photon counting sensor is used and is also a front-view diagram showing the front view of the detection section having a configuration in which a non-spherical surface lens is placed at a location shifted from a light convergence point of a light convergence optical system and the photon counting sensor is placed at a stage following the lens.
Figure 7C:
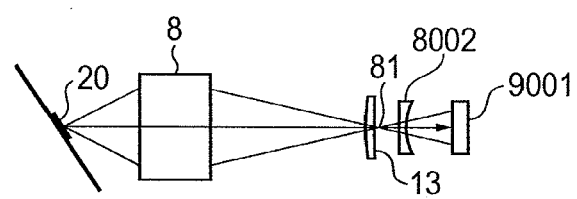
FIG. 7C is a diagram showing a typical configuration of a detection section for a case in which a photon counting sensor is used and is also a front-view diagram showing the front view of the detection section having a configuration in which a plurality of prisms are placed at a location shifted from a light convergence point of a light convergence optical system and the photon counting sensor is placed at a stage following the prisms.
Figure 8:
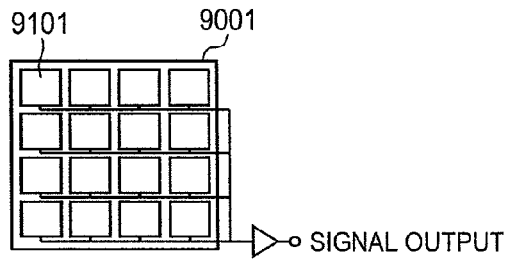
FIG. 8 is a front-view diagram showing the configuration of a photon counting type photosensor.

FIGS. 7A to 7C show typical configurations of the detection section 102a making use of a photon counting sensor. In this case, as a configuration corresponding to that shown in FIG. 3A, configurations making use of a photon counting sensor are shown. However, configurations corresponding to those shown in FIG. 3B to 3D can also be provided by making the same changes as that shown in FIG. 3A. Their explanations are omitted from the following description. Reference numeral 9001 denotes a photon counting sensor. It is necessary to radiate light as uniformly as possible to this sensor. FIG. 8 shows a more concrete configuration of the photon counting sensor 9001. In the photon counting sensor 9001, a number of pixels 9101 are created. When a photon hits any of the pixels 9101, electric charge accumulated in electric-charge accumulation means (not shown in the figure) employed in each of the pixels 9101 is discharged to output a pulse signal. Thus, even if 2 or more photons hit 1 pixel at the same time, only one pulse is output. In addition, once a pulse is output from a pixel, no more pulses are output from the pixel as long as no electric charge is accumulated in the electric-charge accumulation means of the pixel through an electric charging operation or, even if another pulse is output, the strength of the pulse decreases undesirably. Thus, the configuration needs to be set so that photons hit the same pixel as rarely as possible.

Thus, in the configuration shown in FIG. 7A, the photon counting sensor 9001 is provided at a location shifted away from the light convergence point 81 of a light convergence system 8. In the case of such a layout, however, the light quantity distribution in the photon counting sensor 9001 is undesirably a Gauss distribution so that it is difficult to say that the light is radiated uniformly. Thus, in the configuration shown in FIG. 7B, a non-spherical surface lens 8001 is provided so that light is radiated to the photon counting sensor 9001 uniformly. The non-spherical surface lens 8001 is merely used to make an image uniform in the photon counting sensor 9001. The image is an image of scattered light and created on the sample as an image generally having a line shape. In place of a non-spherical surface lens, it is also possible to make use of a diffraction optical device.

In addition, in the configuration shown in FIG. 7C, in place of the non-spherical surface lens 8001, a plurality of prisms 8002 are used. FIG. 7C corresponds to the structure seen from only the horizontal direction, two prisms are seen. However, four prisms may be used. As an alternative, it is also possible to make use of an optical block with a shape having beam optical axes changing at different positions on the optical path.

By making use of the prisms 8002 light guided to the photon counting sensor 9001 through each of the prisms 8001 is refracted when leaving the prism 8001 so that the optical axis direction is shifted. Thus, a distribution having a Gauss-beam peak position shifted on the surface of the photon counting sensor 9001 is superposed thereon so that the peak strength decreases. As a result, the uniformity of the light quantity on the sensor surface is improved. In addition, in place of these, a homogenizer or the like can be used to form an all but uniform illumination strength distribution.

In addition, the configuration shown in either of FIGS. 7A to 7C also includes a polarization filter 13 for reducing the light quantity on the side of the light convergence system 8 with respect to the light convergence point 81 and a mechanism for taking in and out the polarization filter 13. The polarization filter 13 can be taken in and out in accordance with the light quantity. The polarization filter 13 is used for preventing the sensitivity from deteriorating due to an increase of a photon count in the photon counting sensor 9001 to be described later.

The following description explain merits in inspection making use of the photon counting sensor 9001 by comparison with a case in which a photomultiplier tube is used to serve as a detector.

Eq. (1) expresses the minimum amount of light that can be detected by making use of a photomultiplier tube.

$$ENI = (2e \cdot Id \cdot \mu \cdot B)^{1/2} / S(W) \quad (1)$$

In the above equation, reference symbol e denotes electric charge of an electron, reference symbol Id denotes an anode dark current, reference symbol $\mu$ denotes a gain, reference symbol B denotes a cutoff frequency of a detection signal system and reference symbol S denotes an anode radiant sensitivity.

As scattered light generated by a defect is becoming weak, the defect cannot be recognized unless the gain $\mu$ is increased. If the gain $\mu$ is increased in a photomultiplier tube, however, as is commonly known, the dark-current noises also rise so that the S/N ratio decreases. Thus, in the case of using a photomultiplier tube, there is a limit to detection of a small light quantity at a high speed. In addition, there is also a problem that the photomultiplier tube is relatively weak in withstanding magnetic noises.

In the case of using a photon counting sensor, on the other hand, the multiplication factor of the light is determined by the amount of electric charge accumulated in electric-charge accumulation means employed in each pixel. Thus, the multiplication factor can be raised independently of the energy of the incident photon. Accordingly, in the photon counting type sensor 9001, the dark-current noises by no means increase even if the signal becomes weak. In the case of a photon counting sensor, however, if the area of the sensor is increased, the dark-current noises also rise as well. It indicates that, if the number of pixels increases, the dark-current noises also rise as well. That is to say, the dynamic range and the dark-current noises are in a trade-off relation.

Next, the inspection mode of the defect inspection device is explained as follows.

In a defect inspection device, the inspection time and the inspection sensitivity are generally in a trade-off relation. Thus, in many cases, at a production start-up of samples, highly sensitive inspection with a long inspection time is carried out in order to identify problems of the manufacturing process. As the manufacturing process is established and a transition to mass production is made, the inspection time is shortened and relatively low sensitivity inspection is carried out. In this defect inspection device, the illumination spot 20 is lengthened in the longitudinal direction, the area which is inspected while the sample 1 is being rotated once is increased and the inspection time is shortened.

In order to improve the sensitivity, it is necessary to increase the amount of scattered light from the defect as much as possible. In order to prevent the sample from being damaged and the characteristic of the defect from changing, however, the amount of the light is restricted. The amount of the light is set so that the light quantity per unit area is approximately fixed. Thus, if the illumination spot 20 is lengthened in the longitudinal direction, the illumination light quantity can be increased so that the amount of scattered light from the sample 1 serving as an object of inspection is also raised as well. Since the amount of scattered light from the sample serving as an object of inspection is different from the defect signal, the scattered light from the sample serving as an object of inspection is called background scattered light.

As a result, as the throughput is increased, the amount of the background scattered light detected by the photon counting sensor 9001 also rises so that many photons of the background scattered light output pulses from pixels. Thus, even if the defect scattered light is incident to a pixel of the photon counting sensor 9001, the probability that a pulse cannot be output rises, lowering the strength of the signal. In order to apply the photon counting sensor 9001 to such a defect inspection device, it is necessary to make use of the photon counting sensor 9001 by reducing the background scattered light. Thus, a polarization filter 13 is used to suppress the background scattered light. In order for the polarization filter 13 to suppress the background scattered light effectively, it needs for the polarization direction of the defect scattered light being different from the polarization direction of the background scattered light. If the polarization direction of the defect scattered light is the same as the polarization direction of the background scattered light, very little defect scattered light is also suppressed at the same time along with the background scattered light. Thus, the sensitivity adversely deteriorates.

In order to increase the amount of scattered light from a small defect on the sample, it is desirable that the illumination light is incident at polarization P. At that time, scattered light from a defect sufficiently small for the wavelength is scattered mainly at a small elevation angle and the polarization direction vibrates in the normal direction of the sample.

Figure 9:
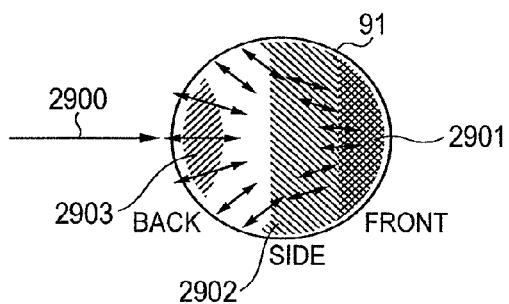
FIG. 9 is a top-view diagram showing the surface of a sample and serving as a diagram to be referred to in explanation of the polarization characteristic of a scattered light distribution from the surface of the sample.

FIG. 9 shows the polarization direction of scattered light at every azimuth. The scattered light is light which is scattered from a sample 1 in directions shown in an rθ coordinate system when illumination light hits the upper surface of the sample 1 in a direction 2900. The center of a circle 91 shown in FIG. 9 shows the normal direction of the scattering light from the sample 1. The distance r from the center of the circle 91 corresponds to an angle (an elevation angle) from the direction normal to the sample 1 whereas the angle θ corresponds to an angle (an azimuth angle) from the incidence direction of the illumination. Reference numeral 2901 denotes front scattered light, reference numeral 2902 denotes side scattered light whereas reference numeral 2903 denotes back scattered light.

The polarization direction of light scattered from a defect is a direction almost normal to the sample. Thus, in the front scattered light 2901, the polarization direction of light scattered from a defect is perpendicular to the polarization direction of light scattered from the sample so that only the background scattered light can be eliminated by making use of the polarization filter 13. In the back scattered light 2903, however, the polarization directions of the defect scattered light and the background scattered light almost coincide with each other. Thus, the background scattered light 2903 cannot be eliminated by making use of the polarization filter 13. In addition, in the side scattered light 2902, an intermediate characteristic between these two above. On the top of that, besides what is described above, if the sample 1 is a silicon wafer for example, due to its polarization characteristic, a phenomenon occurs as follows: the background scattered light is strong in comparison with the front scattered light.

At that time, the polarization filter 13 can be used. Thus, the background scattered light can be made less strong in comparison with the front scattered light 2901 by about 10% to 20%. As a result, in an area with little background scattered light, a defect can be detected. At locations of the side scattered light 2902 and the back scattered light 2903, on the other hand, it is necessary to detect a defect under a condition with much background scattered light.

If the background scattered light quantity is large, rather than dark-current noises advantageous to the photon counting sensor 9001, shot noises caused by the background scattered light serve as a main cause. Thus, instead of reducing the dark-current noises, the shot noises need to be decreased. That is to say, it is important to improve the photon detection efficiency.

Figure 10:
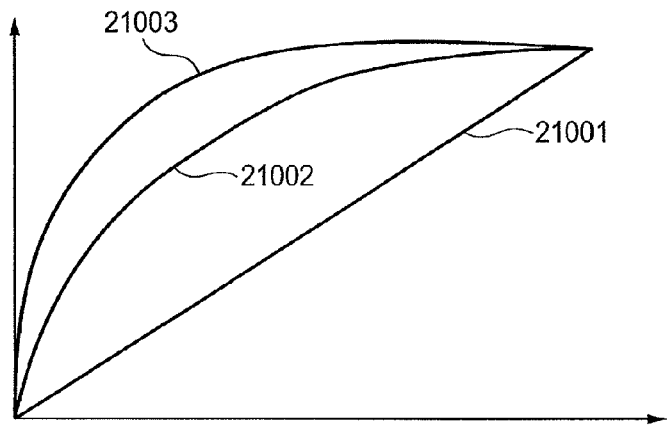
FIG. 10 shows graphs to be referred to in explanation of relations between the incident-light quantity of a photon counting type photosensor and the output of the detector.

FIG. 10 shows detector outputs in the vertical axis for light-quantity inputs in the horizontal axis. Reference numeral 21001 denotes an output characteristic of a photomultiplier tube whereas reference numeral 21002 and 21003 each denote an output characteristic of a photon counting type photosensor. In comparison with the photon counting type photosensor having the output characteristic 21002, the photon counting type photosensor having the output characteristic 21003 is created from many pixels. The photon counting type photosensor having the output characteristic 21003 is capable of obtaining better S/N ratio for small incident light quantities. Since the size of the pixel is large, the ratio of an insensitive area surrounding a pixel to the pixel is small. It can thus be expected that photons are detected with a high degree of efficiency. On the other hand, the photon counting type photosensor having the output characteristic 21002 is created from a number of pixels. Thus, the ratio of an insensitive area surrounding a pixel to the pixel is large. As a result, the shot noise is large and the sensitivity is poor. If the gain is increased in the photon counting type photosensor having the output characteristic 21001, the dark-current noise increases. Thus, the gain cannot be increased. In addition, besides the shot noise and the dark-current noise, a magnetic noise generated by a motor or the like is detected with ease in the defect inspection device. The magnetic noise reduces the sensitivity.

This situation changes in case the incident light quantity increases. In the case of the output characteristic 21001, even if the incident light quantity increases, the relation between the output and the incident light quantity is linear. In the case of the output characteristic 21002 and the output characteristic 21003, however, the probability that a plurality of photons hit a pixel increases so that, even if the incident light quantity increases, the output does not rise that much. This brings about the same effect as reducing photon detection efficiency and causes reducing the S/N ratio in detecting defects. The figure shows characteristics in which, in the first place, the output characteristic 21003 decreases and, then, the output characteristic 21002 decreases. In an area with a large light quantity, the output characteristic 21001 is best.

Due to such characteristics, for the photomultiplier tube, the performance of the photon counting type photosensor changes much in accordance with whether the background scattered light is strong or weak. In the case of weak background scattered light, due to the aperture ratio and the high gain, the performance of the photon counting type photosensor with relatively few pixels is good. As the background scattered light increases, the performance of the photon counting type photosensor with relatively large number of pixels and having a performance of the photon counting type photosensor with a low gain and a low aperture ratio is good. In addition, if the background scattered light increases further more, the performance of the photomultiplier tube is good. Thus, in a defect inspection device for inspecting samples having a variety of types by making use of different illumination light quantities, in order to increase the sensitivity, it is important to provide photon counting type photosensor having different pixel counts and a photomultiplier tube as a combination.

In a case the background light quantity is small, when the scattered light quantity from the defect itself increases so that the detection efficiency of the photon counting type photosensor decreases and causing deterioration of the S/N ratio, even if it happens, the reduction of the S/N ratio does not much affect the defect detection. This is because defect scattered light with a sufficient quantity has already been incident in the photon counting type photosensor. A problem is raised if the amount of background scattered light increases. The amount of the background scattered light can be reduced by making use of a polarization filter 13 at the position of the front scattered light 2901. Thus, a photon counting type photosensor having the characteristic 21003 can be used there. At the position of the side scattered light 2902, on the other hand, as a whole, the sensitivity can be improved by making use of a photosensor having the output characteristic 21003 or the output characteristic 21002. By the same token, at the position of the back scattered light 2903, as a whole, the sensitivity can be improved by making use of a photosensor having the output characteristic 21002 or the output characteristic 21001.

Next, defect dimension estimation and defect classification are explained. In order to estimate the dimension of a defect with a high degree of accuracy, it is necessary to accurately find the defect scattered light quantity obtained in every photosensor. If a photosensor undesirably gets saturated, however, it is no longer possible to find the defect scattered light quantity with a high degree of accuracy.

Figure 11:
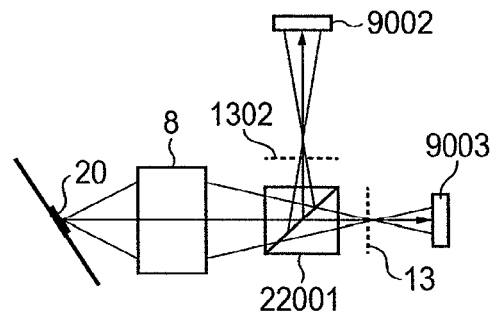
FIG. 11 is a front-view diagram showing the front view of a detection optical system having a configuration which makes use of 2 photon counting type photosensors and can be adapted to also an application with a large scattered light quantity.

In order to solve this problem, a configuration like one shown in FIG. 11 is adopted. The configuration shown in FIG. 11 is used to prevent the photosensor from saturation in the configuration shown in FIG. 7A from getting saturated. Reference numerals 9002 and 9003 each denote a photon counting type photosensor. Reference numeral 22001 denotes a beam splitter for splitting a beam unequally. For example, the beam splitter 22001 splits an input beam into output beams propagating to the photon counting type photosensor 9002 and the photon counting type photosensor 9003 at a ratio of 1:16. In this case, the photon counting type photosensor 9002 is saturated at a relatively small light quantity but the photon counting type photosensor 9003 is not saturated. Thus, an accurate light quantity can be found. As an alternative, it is possible to adopt a configuration employing a photomultiplier tube in place of the photon counting type photosensor 9003 in order to avoid saturation.

Even if the photon counting type photosensor 9003 is not saturated, as shown in FIG. 10, nonlinear output characteristics exist. It is thus necessary to compute a scattered light quantity on the basis of the nonlinear output characteristic. In order to estimate a scattered light quantity, the signal processing section 105 is provided with a table for computing a scattered light quantity from a signal output from the photosensor. In place of such a table, an approximation formula can also be used. Let reference symbol f denote an equation for inferring a scattered light quantity from this output value. In this case, the defect scattered light quantity is expressed by Eq. 2 given as follows.

$$I = \sum_i f_i(x) - \overline{\sum_i f_i(x)} \quad (2)$$

$$\approx \sum_i f_i(x) - \sum_i \overline{f_i(x)}$$

In the above equation,
X: Quantity of light detected by a photon counting type photosensor
X: Time average of quantities of light detected by a photon counting type photosensor As described above, a defect signal obtained in each photosensor and a time average of such defect signals are taken as background scattered light quantities. The time average is found over a sufficiently long period from the sum of background scattered light signals. By making use of the equation f, the defect signal obtained in each photosensor and the background scattered light are transformed into a linear space in order to find a scattered light quantity.

Figure 12:
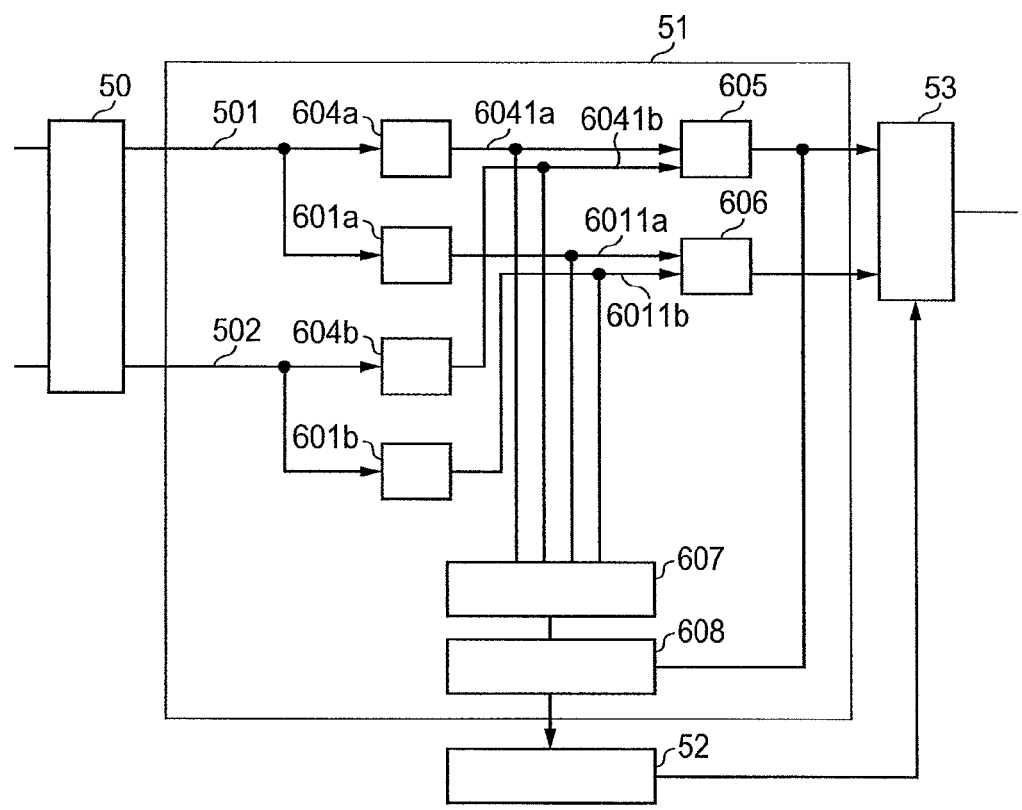
FIG. 12 is a circuit block diagram showing a signal processing section provided by the present invention.

Next, a defect determination section 51 composing the signal processing section 105 is explained by referring to FIG. 12. The following description explains processing for a case in which 2 light detection systems are used. Output signals 501 and 502 from an analog processing section 50 are supplied to high-pass filters 604a and 604b respectively to generate respective defect signals 603a and 603b which are supplied to a defect determination section 605. Since the defect is scanned by the illumination spot 20 in the S1 direction, the waveform of the defect signal enlarges or shrinks an S1-direction illumination profile of the illumination spot 20. Thus, the high-pass filters 604a and 604b each pass a frequency band including the defect signal waveform, blocking a frequency band, which includes relatively numerous noises, and the direct-current component. As a result, the S/N ratios of the defect signals 6041a and 6041b are improved.

Each of the high-pass filters 604a and 604b is a high-pass filter designed to have a specific cutoff frequency and block components having frequencies higher than the cutoff frequency. As an alternative, each of the high-pass filters 604a and 604b can also be a band-pass filter. As another alternative, each of the high-pass filters 604a and 604b can also be a filter for forming a figure similar to the waveform of a defect signal in which the shape of the illumination spot 20 is reflected. The defect determination section 605 carries out threshold-value processing on the input signals 6041a and 6041b including defect waveforms output by the high-pass filters 604a and 604b respectively in order to determine whether or not a defect exists. That is to say, since the defect determination section 605 receives defect signals based on detection signals from a plurality of light detection optical systems, the defect determination section 605 can carry out threshold-value processing on the sum of a plurality of defect signals or a weighted average of the defect signals. As an alternative, the defect determination section 605 can also carry out typically OR or AND processing on a group of defects in the same coordinate system set on the surface of a wafer and performs defect inspection with a very high degree of sensitivity comparing to the result of the OR or AND processing with defect detection based on a single defect signal.

Then, for a position at which a defect has been determined to exist, the defect determination section 605 outputs defect coordinates as information on the defect. The defect coordinates are a defect position in the wafer. The defect position is computed on the basis of a defect waveform and a sensitivity information signal.

As described above, the analog processing section 50 generates the output signals 501 and 502. The output signal 501 is supplied to the high-pass filter 604a and a low-pass filter 601a whereas the output signal 502 is supplied to the high-pass filter 604b and a low-pass filter 601b. The high-pass filter 604a, the low-pass filter 601a, the high-pass filter 604b and the low-pass filter 601b are employed in the defect determination section 51. The low-pass filters 601a and 601b each output low-frequency components and the direct-current component. The low-frequency components and the direct-current component are components of a scattered light quantity (haze) from minute roughness in the illumination spot 20 on the wafer 1. The low-pass filters 601a and 601b supply outputs 6011a and 6011b respectively to a haze processing section 606 for carrying out haze information processing. That is to say, the haze processing section 606 outputs a haze signal indicating the magnitude of a haze for each location on the wafer 1. The haze signal is a signal computed from the magnitudes of the input signals 6011a and 6011b received from the low-pass filters 601a and 601b respectively. In addition, in accordance with a spatial frequency distribution of minute roughness, an angle distribution of light scattered from the roughness changes. Thus, as shown in FIG. 1, haze signals are used as inputs to the haze processing section 606 from detectors of a plurality of light detection sections 102 provided at locations with azimuths different from each other and elevation angles also different from each other. By making use of haze signals as inputs to the haze processing section 606, it is possible to obtain information on the spatial frequency distribution of little roughness from, among others, strength ratios computed by the haze processing section 606.

Reference numeral 607 denotes a storage section used for temporarily storing outputs of all detectors, such as the outputs 6041a and 6041b of the high-pass filters 604a and 604b respectively as well as the outputs 6011a and 6011b of the low-pass filters 601a and 601b respectively. Reference numeral 608 denotes a storage section for storing information on a defect data determined as a defect in the defect determination section 605. By storing only the defect data and the quantity of scattered light from the sample 1, it is possible to prevent the size of the storage section 608 from increasing.

Reference numeral 52 denotes a defect-size-inference/defect-classification section for correcting nonlinearity of the output from the photon counting sensor 9001 in order to estimate a correct defect size and to classify defects. An estimated size and a defect classification result are supplied to an entirety control section 53 to be output to a display section 54 or the like.

The defect-size-inference/defect-classification section 52 computes defect coordinates on the basis of the center of gravity of a defect waveform. A defect dimension is calculated on the basis of an integration value of the defect waveform or its maximum value. If a saturated signal magnitude or a signal magnitude close to a saturation value has been obtained in a specific detector, the quantity of scattered light is computed on the basis of outputs of detectors other than the specific detector which has been saturated.

Figure 13:
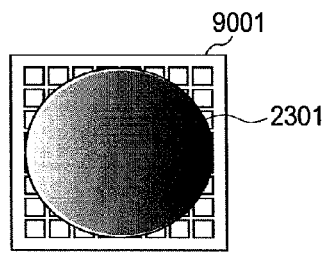
FIG. 13 is a front-view diagram showing the front view of a photon counting type photosensor and serving as a diagram to be referred to in explanation of an illumination state of light reflected to the photon counting type photosensor.

The following description explains a system for computing a detected scattered light quantity from detection signals of detectors. FIG. 13 is a model diagram showing a photon counting sensor 9001 for detecting scattered light. Reference numeral 2301 denotes a strength distribution of scattered light.

The strength distribution of scattered light from the sample and the distribution of scattered light from a defect do not necessarily provide a state in which strengths are uniform. In such a state, scattered light hits the photon counting sensor 9001. The distribution of this scattered light may change in some cases in accordance with the type of the sample and the polarization condition of the illumination. Desirably, it is necessary to find a way to compute the brightness from the output of the detector for every scanning condition. Thus, the following information is stored. The information includes outputs which are obtained when every photon counting sensor 9001 detects scattered light from the surface of the sample or a foreign substance. In this case, the detected light is light scattered when the illumination strength is changed by the attenuator 3.

Figure 14:
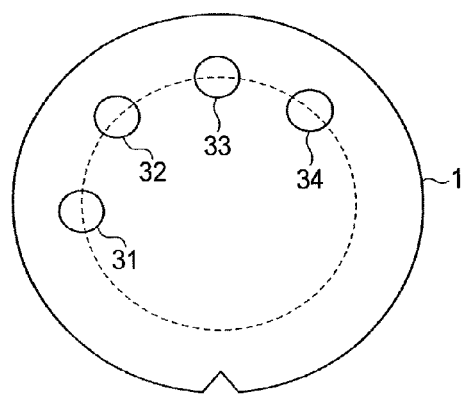
FIG. 14 is a top-view diagram showing the top view of a sample in a state of being mounted to serve as a calibration sample for correcting nonlinearity of the relation between the incident-light quantity of a photon counting type photosensor and the output of the detector.

FIG. 14 shows a sample 1 for calibration. As shown in the figure, standard samples 31 to 34, whose particle diameter sizes are known, are distributed in advance on the sample 1. When illumination light with polarization P is irradiated to the sample 1, it is known that the scattered light quantity is proportional to the 6th power of the particle diameter. In a case that a particle diameter size is sufficiently small in comparison with a wavelength of the illumination light, the radiation direction of the scattered light is all but isotropic.

Figure 15:
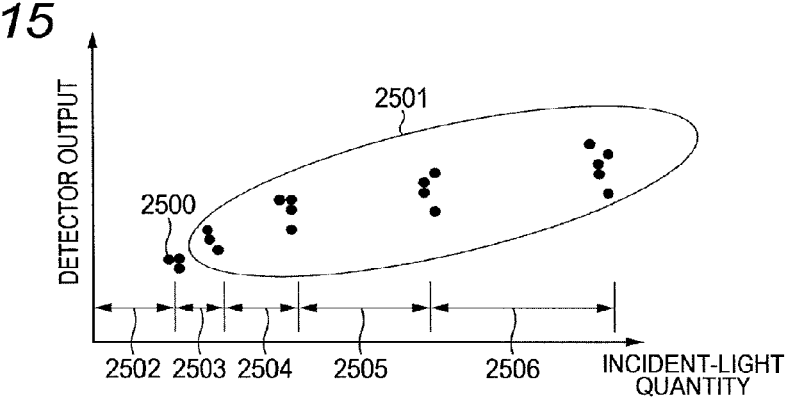
FIG. 15 shows a graph representing an input/output characteristic of a detector obtained by making use of a calibration sample for correcting nonlinearity of the relation between the incident-light quantity of a photon counting type photosensor and the output of the detector.

This sample is used for obtaining different incident light quantities. When the incident light quantity is changed, the photon counting type photosensor detects scattered light from the sample and the standard particles, generating outputs which are shown in FIG. 15. Reference numeral 2500 denotes an output signal which is generated by the photon counting type photosensor 9001 when the photon counting type photosensor 9001 detects scattered light from the surface of the sample. Output signals in an area enclosed by a line 2501 are outputs which are generated by the photon counting type photosensor 9001 when the photon counting type photosensor 9001 detects scattered light from a particular area on the sample 1. The particular area is an area in which the standard particles 31 to 34 whose particle diameter sizes are known have been distributed in advance. If the incident light quantity of the illumination is small, the output signal 2500 generated by the photon counting sensor 9001 is considered to be about equal to an actual photon incidence quantity. Thus, an incident light quantity 2502 is obvious. However, gaps representing incident light quantities 2503 to 2506 are not necessarily obvious. Since the scattered light quantity is proportional to the 6th power of the particle diameter, however, ratios of the gaps representing incident light quantities 2503 to 2506 are known.

An output Oi generated by the photon counting sensor 9001 is ideally expressed by Eq. 3 given as follows:

$$O_i = A_i(1 - P_i^{N_i}) \tag{3}$$

Eq. 3 is changed to Eq. 4 given as follows:

$$N_i \log P_i = \log(A_i - O_i) \tag{4}$$

Unknown variables in the above equation are explained as follows. Reference symbol $N_i$ denotes a quantity of incident light hitting a photon counting type photosensor i. The light hitting the photon counting type photosensor i corresponds to output signals of an area enclosed by the line 2501. Reference symbol $P_i$ denotes a probability that photons are incident to pixels other than a certain specific pixel. Reference symbol $\log P_i$ denotes the logarithmic value of the probability $P_i$. If the incident light quantity $N_i$ is multiplied by K, in Eq. 4, an equation obtained by different incident light quantities $N_i$ is derived. Thus, $\log P_i$ can be found from simultaneous equations. Since it is not necessarily the output ideally expressed by Eq. 3, however, measurement making use of an illumination strength is carried out a plurality of times. Then, parameters are found by adoption of the least square method or the like in order to compute a corrected curve.

Figure 16:
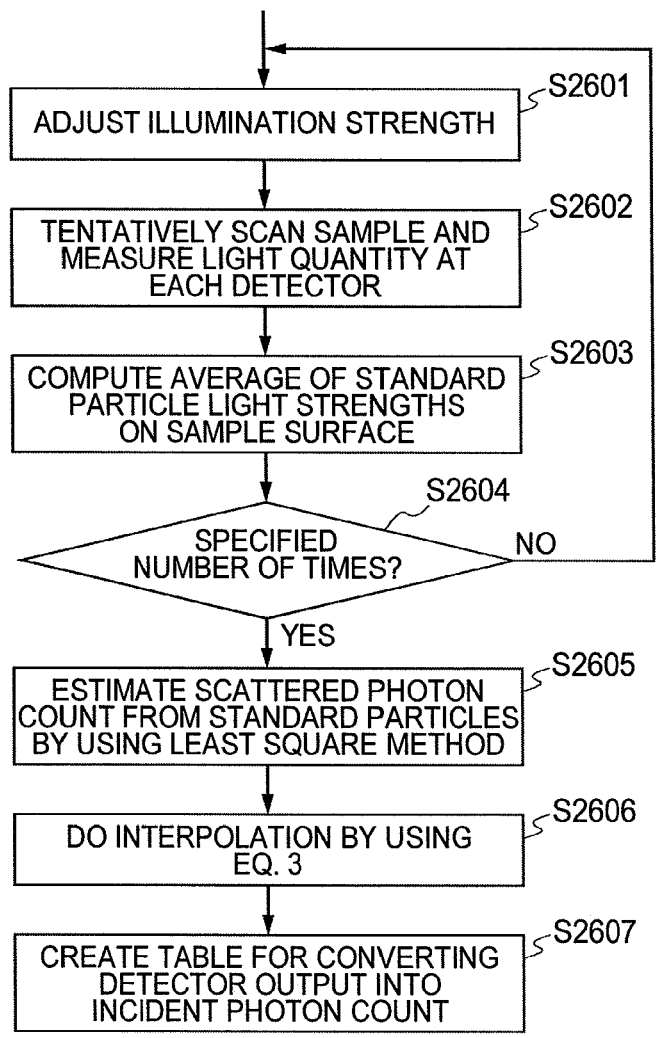
FIG. 16 is a flowchart showing a nonlinearity measurement sequence executed by making use of a calibration sample for correcting nonlinearity of the relation between the incident-light quantity of a photon counting type photosensor and the output of the detector.

This sequence is explained by referring to FIG. 16. First of all, at a step S2601, an illumination strength is determined. Then, at a step S2602, the sample 1 is inspected and a signal output by every photon counting sensor 9001 detecting scattered light from the surface of the sample 1 and the standard particles is stored. Then, at a step S2603, representative scattered light strengths of the surface of the sample 1 or the standard particles are computed. The representative scattered light strengths include typically an average value, a median value, or a peak value, which are each a value computed from the scattered light strengths of the surface of the sample 1 and the standard particles.

Then, the sequence goes on to a step S2604 to determine whether or not the processing described above has been carried out a predetermined number of times. If the processing described above has not been carried out the predetermined number of times, the sequence goes back to the step S2601 to change the illumination strength and inspect the sample 1 again in order to obtain an output signal of each photon counting sensor 9001. If the processing to obtain data has been carried out the predetermined number of times, on the other hand, the sequence goes on to a step S2605 at which the least square method is adopted to compute the unknown variable log P and estimate an incident light quantity on the basis of the variable log P. The incident photon quantity is the quantity of photon hitting every photon counting sensor 9001 from the surface of the sample 1 and the standard particles for each illumination strength.

Then, at a step S2606, the incident light quantity and the output of the photon counting type photosensor (light detector) 9001 are computed by making use of a conversion formula expressed by Eq. 3. In this case, since log P actually varies in accordance with the incident light quantity (In actuality, an ideal curve is not obtained due to, among others, differences in scattered strength distribution inside the lens), for each quantity, the value of P is newly set by making use of its close light quantity data in interpolation so that the value of P corresponds to actual data. Then, the sequence goes on to a step S2607 to create a table for converting the output of each photon counting sensor 9001 into an incident photon count.

As described above, the quantity of light incident to every photon counting sensor 9001 can be found. However, the estimated precision of the incident light quantity obtained by each photon counting sensor 9001 varies. That is to say, if the output of the photon counting sensor 9001 also substantially changes when the detected light quantity changes, high estimation precision of the incident light quantity is required. Processing carried out by the defect determination section 605 is explained as follows.

In the photon counting sensor 9001, the first deviation of the output of the photon counting sensor 9001 changes for a case in which the brightness changes due to the incident light quantity. Thus, the photon counting sensor 9001 for finding the incident light quantity changes with the light quantity. For this reason, estimation of the defect size is explained.

If noises are assumed to be quantization noises when the sum of signals output by all the photon counting type photosensors 9001 is computed, the sum can be computed by multiplying the signals output by the photon counting type photosensors 9001 by weights which are proportional to signal strengths detected by the photon counting type photosensors 9001 but inversely proportional to background scattered light. In this way, the ratio of the defect signal to noises can be maximized. This is expressed by Eq. 5 given as follows.

$$O_{all} = \sum_i g_i O_i = \sum_i g_i(\overline{O_i} + \Delta_i) = \sum_i g_i(\overline{O_i} + s_i + n_i) \quad (5)$$
$$= \sum_i g_i(\overline{O_i} + \omega_i ls_i + \omega_i ln_i)$$

With regard to the nonlinearity of the photon counting sensor 9001, an actual aperture ratio of the detector i can be regarded to have decreased to $g_i$ times a reference aperture ratio of the detector i. In this case, the actual aperture ratio is an aperture ratio for a case in which background scattered light increases and a photon hits a pixel already generating an output. On the other hand, the reference aperture ratio is an aperture ratio for a case in which the detected light quantity is 0.

In Eq. 5, reference symbol $s_1$ denotes the strength of a defect scattered signal whereas reference symbol $n_i$ denotes a noise scattered signal. Both are frequency components. Reference symbol $\omega_i$ corresponds to a derivative value of the output of the photosensor for light which is incident when the light quantity to be detected is 0. The derivative value $\omega_i$ is expressed by a gradient at an incident light quantity of 0 on a graph shown in FIG. 15. The graph represents a relation for the incident light quantity of the photon counting type photosensor. Reference symbols $ls_i$ and $ln_i$ denote a defect scattered light signal component and a noise component, respectively.

Reference symbol $O_{all}$ denotes a sum obtained by integration of signals output by the photosensors. From Eq. 5, it is obvious that the sum $O_{all}$ is regarded as a sum obtained by multiplying each of the signals by a gain $g_i \omega_i$. $g_i$ changes in accordance with the quantity of light incident to the photosensor. In this case, however, the signals are integrated to result in the sum $O_{all}$. Thus, by making use of the sum $O_{all}$ only, gi cannot be determined so that it is difficult to find the particle diameter of the defect. In order to solve this problem, after a defect has been determined, it is necessary to store signals output by the photosensors so that the photosensor signals which have been used in the computation of the sum $O_{all}$ can be referred to. In order to implement this configuration, storage sections 607 and 608 are used. After a defect has been determined, the photosensor signals stored in the storage sections 607 and 608 are referred to in order to compute the quantity of light incident to each photosensor by making use the formula expressed by Eq. 2. Thus, a defect dimension can be computed.

A flowchart of the processing described above is shown in FIG. 17.

First of all, at a step S2701, for scattered light of a position at which a defect has been determined, a signal passing through a high-pass filter is read out from the storage section 608. Then, at a step S2702, for scattered light of the position at which a defect has been determined, a signal passing through a low-pass filter is read out from the storage section 608. Then, at a step S2703, the output of the photon counting type photosensor at the position at which a defect has been determined is found from these 2 signals. Then, the quantity of light received by the photosensor is computed by making use of the table computed at the step S2607. Then, at a step S2704, the background output of the photon counting type photosensor at the position at which a defect has been determined is found. Then, the quantity of light received by the background of the photosensor is computed also by making use of the table computed at the step S2607. From the difference between the light quantities found at the steps S2703 and S2704, the quantity of light received by the photosensor from the defect is found. Then, a step S2706 is executed to set a repetition processing control section employed in the defect inspection device to control all the photosensors to carry out the processing from the step S2701 to the step S2705 or control photosensors sufficiently received scattered light to carry out the processing from the step S2701 to the step S2705.

Then, the flow of processing goes on to a step S2707 to find the sum of defect received-light quantities computed by the photosensors. Then, at a step S2708, the dimension of the defect is computed on the basis of these received-light quantities. If the dimension of the defect is small in comparison with the wavelength, the dimension of the defect is estimated on the basis of the fact that the defect scattered light quantity is proportional to the square of the volume of the defect. As an alternative, the dimension of the defect can also be estimated on the basis of a relative ratio to a scattered light quantity detected by a commonly known standard particle.

If this is implemented, however, a big error may be generated in computation of scattered light by a photosensor having a small $g_i\omega_i$. Thus, in different embodiments, a model data vector is used to eliminate the error.

Here, $g_i\omega_i$ is equal to a gradient of the relation shown in FIG. 15 as a relation associating the incident light quantity with the photon counting type photosensor. Thus, $g_i\omega_i$ is computed in advance. For example, the scattered light quantity to be found is expressed by Eq. 6 given as follows:

$$S1 = [1\ 1\ \ldots\ 1][N_1 N_2 \ldots N_n]^T \tag{6}$$

Assume that the sum of outputs actually generated by the photosensors is expressed by Eq. 7 given as follows.

$$S2 = [g_1\omega_1 g_2\omega_2 \ldots g_n\omega_n][N_1 N_2 \ldots N_n]^T \tag{7}$$

In this case, to find outputs of Eq. 6 from detection results of Eq. 7, a model data vector is used.

In order to implement this, in a state in which the light quantity of the illumination is small, that is, in a state in which the photon counting type photosensor has not been saturated, the quantity of light incident to the photosensor is computed in advance from the obtained output of the photosensor. Then, vectors $[N_1 N_2 \ldots N_n]$ shown in Eq. 7 are computed to be used as a model data vector $M_n$.

Here, an output S2/S1 varying due to the transformation from Eq. 6 to Eq. 7 is expressed by Eq. 8 given as follows.

$$S2/S1 = [g_1\omega_1 g_2\omega_2 \ldots g_n\omega_n]M_n^T/[1\ 1\ \ldots\ 1]M_n^T \tag{8}$$

By multiplying this reciprocal, it is possible to obtain an output with a corrected difference in sensitivity among photosensors.

When the photon counting type photosensor starts getting saturated, the value of Eq. 8 changes. By computing the reciprocal of this value, it is possible to correct a difference in sensitivity between photosensors.

Figure 18:
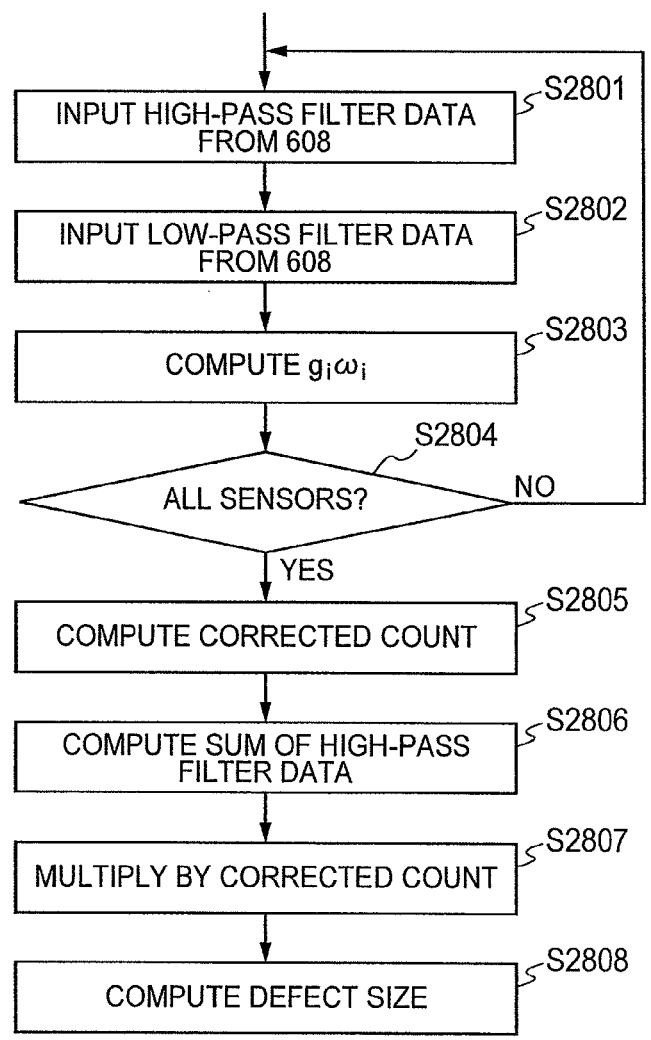
FIG. 18 is a flowchart showing a flow of processing carried out to compute the quantity of scattered light by converting output values of a photon counting type photosensor on the basis of a model data vector without directly converting the output values.

As above, without actually computing the detected light sensitivity of this sensor by directly converting the output of the photon counting type photosensor, it is possible to compute the scattered light quantity to be determined by converting the output on the basis of a model data vector. The flowchart is shown in FIG. 18. Processing carried out at steps S2801, S2802, S2804 and S2808 is not explained here since that is the same as the processing carried out at steps S2701, S2702, S2706 and S2708 respectively. Only processing unique to the flowchart shown in FIG. 18 is explained.

Figure 17:
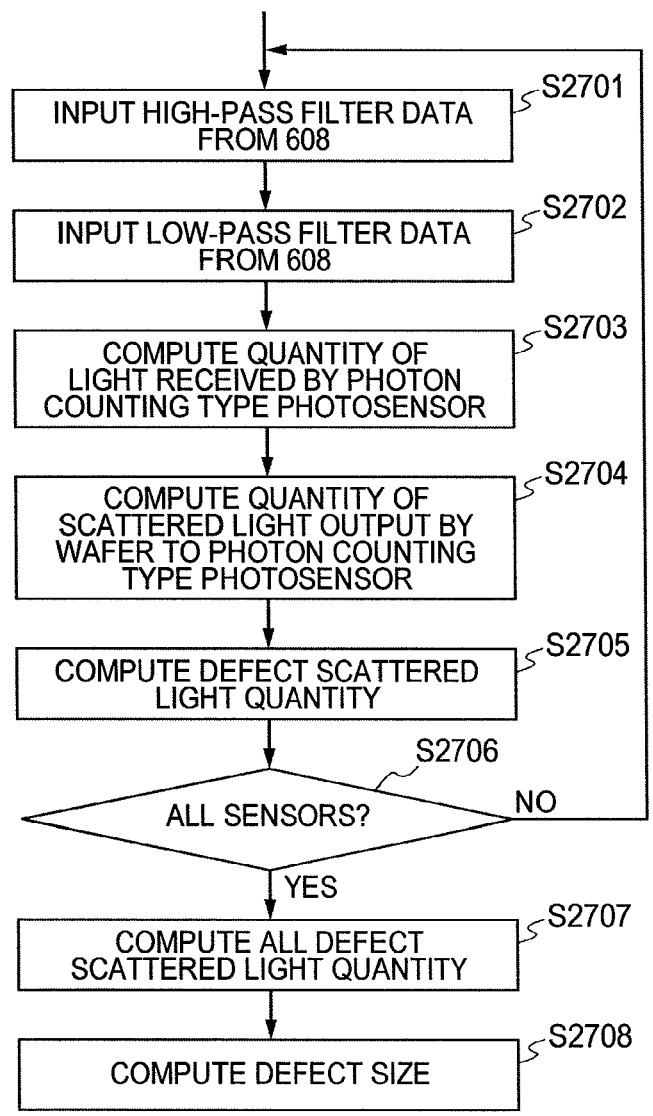
FIG. 17 is a flowchart showing a flow of processing carried out to compute the quantity of light incident to each detector, find a total light quantity of light scattered by a defect and calculate the dimensions of the defect.

In the processing shown in FIG. 17, the quantity of light received by a photosensor is computed for every photosensor. In the processing shown in FIG. 18, however, $g_i\omega_i$ is computed at a step S2803. Here, $g_i\omega_i$ is a gradient between an incident light quantity of the photon counting type photosensor and the output of the photosensor. The incident light quantity is a quantity computed by interpolation at the step S2606 at an operating point of the output value of each photosensor. After this has been repeated number of times equal to the number of the photosensors, the value of expression 9 expressing correction coefficients is computed at a step S2805.

$$[g_1\omega_1 g_2\omega_2 \ldots g_n\omega_n]M_n^T/[1\ 1\ \ldots\ 1]M_n^T \tag{9}$$

Then, the sum of output values generated by high-pass filters for outputs of the photosensor is computed at a step S2806. Then, at a step S2807, the outputs computed at the step S2806 are each multiplied by a correction coefficient calculated at the step S2805. The product is taken as the scattered light quantity from a defect from which light is received by all the photosensors. Then, at a step S2808, for this scattered light quantity, the dimension of the defect is computed by carrying out the same processing as that performed at the step S2708 of the flowchart shown in FIG. 17.

In accordance with this embodiment, it is possible to detect both a small defect generating only weak scattered light and a deformed defect generating scattered light only at the rear location.

The present invention innovated by the inventors has been explained above in concrete terms on the basis of an embodiment. However, the scope of the present invention is not limited to the above embodiment. Of course, it is possible to make a variety of changes within a range not deviating from essentials of the present invention.

REFERENCE SIGNS LIST

1 . . . Wafer,
2 . . . Laser light source,
3 . . . Attenuator,
4 . . . Polarization device,
5 . . . Illumination distribution control device,
6 . . . Convergence lens,
7 . . . Beam expander,
8 . . . Light convergence system,
9 . . . Sensor,
10 . . . Parallel-movement stage,
11 . . . Rotation stage,
13 . . . Polarization filter,
14 . . . Controller,
15 . . . Light blocking shutter,
16 . . . Shutter controller,
20 . . . Illumination spot,
31 . . . Standard particle coating area,
50 . . . Analog processing section,
51 . . . Defect determination section,
52 . . . Defect-size-inference/defect-classification section,
53 . . . Entirety control section,
54 . . . Display section,
55 . . . Input section,
101 . . . Illumination section, 102a . . . Detection section,
102b . . . Detection section,
102c . . . Detection section,
103 . . . Stage section,
104 . . . Regular reflection detection section,
105 . . . Signal processing section.

The invention claimed is:

1. A defect inspection device, comprising:
an illumination optical unit which illuminates a sample with a laser beam from a oblique direction;
a detection optical unit which detects light diffracted from the sample illuminated with the laser beam by the illumination optical unit; and
a signal processing unit which detects a defect on the sample by processing an electrical signal generated by detecting the light diffracted from the sample with the detection optical unit,
wherein, the detection optical unit installs plural detectors including a photon counting type detector having plural pixels, the plural detectors including a front detector which detects forward-scattered light which scattered in forward direction to a illumination direction of the laser beam to the sample by the illumination optical unit and a backward detector which detects back-scattered light which scattered in backward direction to a illumination direction of the laser beam to the sample by the illumination optical unit, and a pixel number of the front detector is larger than that of the backward detector so that a photon detection efficiency of the front detector is higher than a photon detection efficiency of the backward detector.

2. The defect inspection device according to claim 1, wherein the detection optical unit installs a polarizing filter between one of the plural detectors and the sample and cut off a light in a direction perpendicular to a light scattered from the sample.

3. The defect inspection device according to claim 1, wherein the detection optical unit installs a bean splitter between one of the plural detectors and the sample and a detector which detects a light form the sample and branched by the beam splitter.

4. The defect inspection device according to claim 1, wherein at least one of the plural detectors is an analog type detector and the front detector is a photon counting type detector.

5. A method of inspecting a defect, including the steps of:
radiating a laser beam onto a sample from an oblique direction through an illumination optical unit;
detecting a scattered light from the sample on which the laser beam is radiated, with a detection optical unit; and
detecting a defect on the sample by processing an electrical signal output from the detection optical unit by the detection of the scattered light, with a signal processing unit,
wherein, in the step of detecting the scattered light from the sample, the scattered light is detected by plural detectors including photon counting type detector, and among the plural detectors a forward-scattered light which scattered in forward direction to a illumination direction of the laser beam to the sample by the illumination optical unit is detected by a front detector and back-scattered light which scattered in backward direction to a illumination direction of the laser beam to the sample by the illumination optical unit is detected by a backward detector, and the front detector detects the forward-scattered light with sensors a pixel number of which is larger than that of the backward detector so that a photon detection efficiency of the front detector is higher than a photon detection efficiency of the backward detector.

6. The method of inspecting a defect according to claim 5, wherein in the step of detecting the scattered light with the detection optical unit, the scattered light is detected through a polarizing filter installed between one of the plural detectors and the sample and which cut off a light in a direction perpendicular to a light scattered from the sample.

7. The method of inspecting a defect according to claim 5, wherein in the step of detecting the scattered light with the detection optical unit, one of the forward-scattered light or the back-scattered light is branched by a beam splitter and detected.

8. The method of inspecting a defect according to claim 5, wherein at least one of the plural detectors of the detection optical system is an analog type detector and the front detector is a photon counting type detector.

* * * * *